(12) United States Patent
Wazni et al.

(10) Patent No.: US 11,896,281 B2
(45) Date of Patent: Feb. 13, 2024

(54) CRYO-FIXATION CARDIAC PACEMAKER LEAD EXTRACTION DEVICE

(71) Applicants: THE CLEVELAND CLINIC FOUNDATION, Cleveland, OH (US); CPSI Holdings, LLC, Owego, NY (US)

(72) Inventors: Oussama Wazni, Bentleyville, OH (US); Marwane Berrada-Sounni, Beachwood, OH (US); John M. Baust, Candor, NY (US); Kristi K. Snyder, Candor, NY (US)

(73) Assignees: THE CLEVELAND CLINIC FOUNDATION, Cleveland, OH (US); CPSI HOLDINGS LLC, Owego, NY (US)

( * ) Notice: Subject to any disclaimer, the term of this patent is extended or adjusted under 35 U.S.C. 154(b) by 1316 days.

(21) Appl. No.: 16/185,577

(22) Filed: Nov. 9, 2018

(65) Prior Publication Data

US 2019/0142495 A1    May 16, 2019

Related U.S. Application Data

(60) Provisional application No. 62/584,191, filed on Nov. 10, 2017.

(51) Int. Cl.
*A61B 18/02* (2006.01)
*A61N 1/05* (2006.01)
(Continued)

(52) U.S. Cl.
CPC .... *A61B 18/0218* (2013.01); *A61B 17/32053* (2013.01); *A61B 18/02* (2013.01);
(Continued)

(58) Field of Classification Search
CPC . A61B 18/0218; A61B 18/02; A61B 18/1492; A61B 18/1206; A61B 18/24;
(Continued)

(56) References Cited

U.S. PATENT DOCUMENTS 5,980,515 A * 11/1999 Tu .......................... A61B 18/14
                                                                606/41
8,163,000 B2 * 4/2012 Dobak, III ................ A61F 7/12
                                                               607/104
(Continued)

*Primary Examiner* — Khadijeh A Vahdat
*Assistant Examiner* — Marina Delaney Templeton
(74) *Attorney, Agent, or Firm* — TAROLLI, SUNDHEIM, COVELL & TUMMINO L.L.P.

(57) ABSTRACT

A cryo-fixation lead extraction device includes a lead extraction catheter having longitudinally spaced proximal and distal catheter ends and an elongate catheter lumen. A liner has longitudinally spaced proximal and distal liner ends and an elongate liner lumen. The liner lumen is configured to selectively accept at least part of a lead being extracted longitudinally therethrough. At least a portion of the liner is located circumferentially within and/or circumferentially surrounding the catheter lumen. At least one cryogen supply line extends longitudinally through at least a portion of the liner lumen. The cryogen supply line is configured to place a cryogen fluid source into fluid communication with the distal liner end. The cryogen supply line is configured to selectively generate a patient tissue cooled zone adjacent the distal catheter end. A method of cryo-fixation lead extraction is also provided.

20 Claims, 8 Drawing Sheets

(51) Int. Cl.
*A61B 17/3205* (2006.01)
*A61B 18/00* (2006.01)

(52) U.S. Cl.
CPC .. *A61N 1/0595* (2013.01); *A61B 2018/00196* (2013.01); *A61B 2018/00202* (2013.01); *A61B 2018/00791* (2013.01); *A61B 2018/00922* (2013.01); *A61B 2018/0212* (2013.01); *A61B 2018/0262* (2013.01); *A61N 2001/0578* (2013.01)

(58) Field of Classification Search
CPC .. A61B 2018/0262; A61B 2018/00791; A61B 2018/00839; A61B 2018/00351; A61B 2018/0293; A61B 2018/0212; A61B 2018/00023; A61B 17/32053; A61B 17/3468; A61B 2017/00243; A61N 1/0595; A61N 1/056; A61N 2001/0578

USPC ............... 606/20, 21, 22, 23, 24, 25, 26
See application file for complete search history.

(56) References Cited

U.S. PATENT DOCUMENTS

| | | | |
|---|---|---|---|
| 2004/0243119 A1* | 12/2004 | Lane | A61B 18/02 606/23 |
| 2011/0071427 A1* | 3/2011 | Fischer | A61B 10/02 606/22 |
| 2012/0035584 A1* | 2/2012 | Thompson-Nauman | A61M 25/04 604/506 |
| 2014/0276682 A1* | 9/2014 | Hendrick | A61M 1/84 606/7 |
| 2015/0300569 A1* | 10/2015 | Baust | F17C 1/00 62/50.1 |
| 2016/0206295 A1* | 7/2016 | Kramer | A61B 18/02 |

* cited by examiner

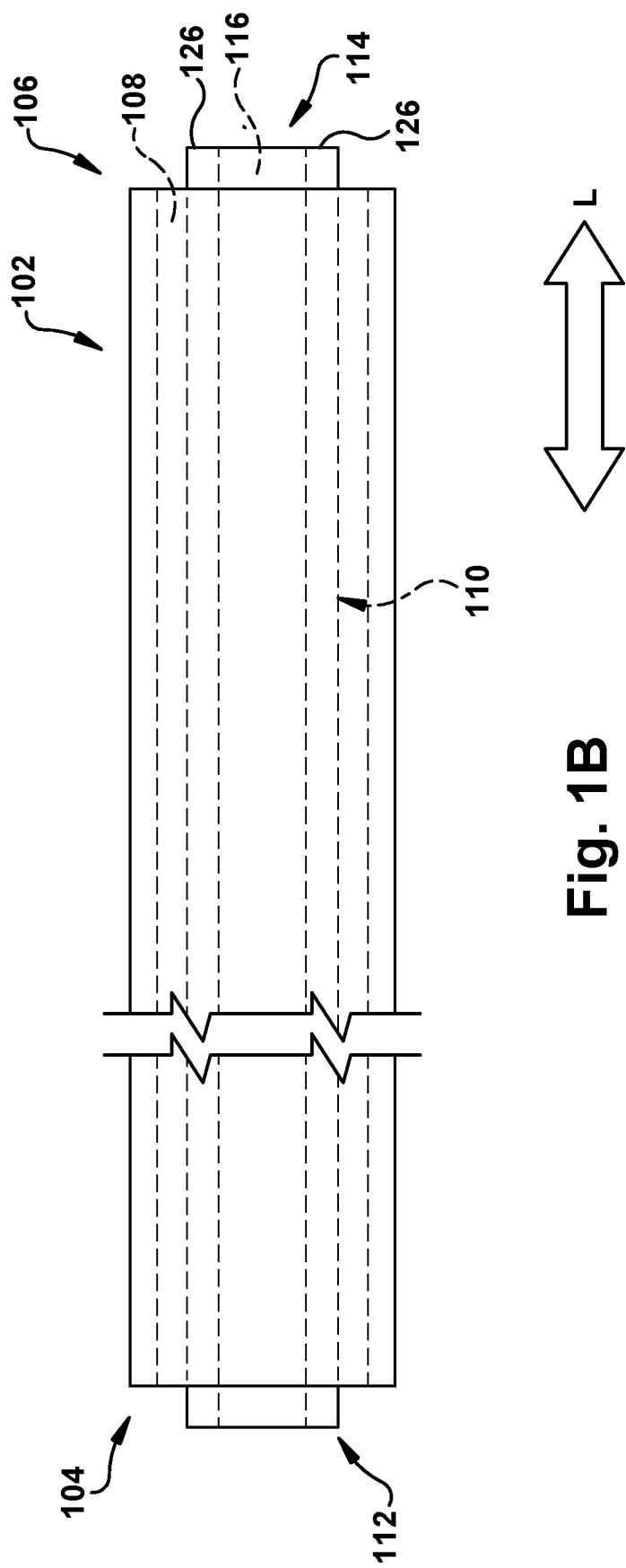

CRYO-FIXATION CARDIAC PACEMAKER LEAD EXTRACTION DEVICE

RELATED APPLICATION

This application claims priority from U.S. Provisional Application No. 62/584,191, filed 10 Nov. 2017, the subject matter of which is incorporated herein by reference in its entirety.

TECHNICAL FIELD

This disclosure relates to an apparatus, system, and method for use of a cryo-fixation lead extraction device and components thereof and, more particularly, to the integration of tissue freezing (cryogenics) into extraction methods for cardiac pacemaker leads and a device for doing such.

BACKGROUND

Leads may be placed for use in connection with, e.g., a cardiac pacemaker, to deliver energy to cardiac muscle. These leads may need to be removed, or extracted, at a later time for any of a number of reasons.

Lead extraction devices typically include a cutting member at a distal tip thereof, which may be movable, e.g., rotatable, and controllable from a trigger or other control on the device. The cutting member may be used to break up scar tissue surrounding the end of the lead, allowing the lead to be freed and removed via a catheter threaded over the lead and guided to the lead tip. The cutting member may take any of a number of forms as desired, but may include, e.g., a metal serrated cutting edge surface.

SUMMARY

In an aspect, a cryo-fixation lead extraction device is provided. A lead extraction catheter has longitudinally spaced proximal and distal catheter ends and an elongate catheter lumen. A liner has longitudinally spaced proximal and distal liner ends and an elongate liner lumen. The liner lumen is configured to selectively accept at least part of a lead being extracted longitudinally therethrough. At least a portion of the liner is located a chosen one of circumferentially within and circumferentially surrounding the catheter lumen. At least one cryogen supply line extends longitudinally through at least a portion of the liner lumen. The cryogen supply line is configured to place a cryogen fluid source which is in operative proximity to the proximal liner end into fluid communication with the distal liner end. The cryogen supply line is configured to selectively generate a patient tissue cooled zone adjacent the distal catheter end.

In an aspect, a cryo-fixation lead extraction system is described, the cryo-fixation lead extraction system including a cryogen fluid source. A cryo-fixation lead extraction device includes a lead extraction catheter having longitudinally spaced proximal and distal catheter ends and an elongate catheter lumen. A liner has longitudinally spaced proximal and distal liner ends and an elongate liner lumen. The liner lumen is configured to selectively accept at least part of a lead being extracted longitudinally therethrough. At least a portion of the liner is located a chosen one of circumferentially within and circumferentially surrounding the catheter lumen. At least one cryogen supply line extends longitudinally through at least a portion of the liner lumen. The cryogen supply line is configured to place a cryogen fluid source which is in operative proximity to the proximal liner end into fluid communication with the distal liner end. The cryogen supply line is configured to selectively generate a patient tissue cooled zone adjacent the distal catheter end. A cryogen regulator is associated with the cryogen fluid source. An operator interface is operatively connected to the cryogen supply line for selectively regulating cryogen fluid flow. A computing device is provided for at least one of controlling and monitoring the cryo-fixation lead extraction device during operation. The computing device includes a user-perceptible display and at least one user-manipulable control.

In an aspect, a cryo-fixation lead extraction liner is described, the cryo-fixation lead extraction liner including longitudinally spaced proximal and distal liner ends and an elongate liner lumen. The liner lumen is configured to selectively accept at least part of a lead being extracted longitudinally therethrough. At least one cryogen supply line extends longitudinally through at least a portion of the liner lumen. The cryogen supply line is configured to place a cryogen fluid source which is in operative proximity to the proximal liner end into fluid communication with the distal liner end. The cryogen supply line is configured to selectively generate a patient tissue cooled zone adjacent the distal liner end.

In an aspect, a method of extracting a lead from a patient tissue volume using cryogenics is described. A cryo-fixation lead extraction device including a lead extraction catheter having longitudinally spaced proximal and distal catheter ends and an elongate catheter lumen is provided. A liner has longitudinally spaced proximal and distal liner ends and an elongate liner lumen. At least a portion of the liner is located a chosen one of circumferentially within and circumferentially surrounding the catheter lumen. At least one cryogen supply line extends longitudinally through at least a portion of the liner lumen. With the cryogen supply line, a cryogen fluid source, which is in operative proximity to the proximal liner end, is placed into fluid communication with the distal liner end. At least part of a lead being extracted is placed longitudinally through the liner lumen. Cryogen fluid is selectively directed from the cryogen fluid source through the cryogen supply line to selectively generate a patient tissue cooled zone adjacent the distal catheter end within the patient tissue volume. Within the patient tissue cooled zone, the lead is loosened from the patient tissue. The loosened lead is moved proximally with respect to the liner lumen.

In an aspect, a cryoconsole is described. A cryogen fluid source is associated with the cryoconsole. A regulator is provided for regulating cryogen flow pressure. A cryogen supply line is provided for carrying cryogen fluid from the cryogen fluid source. A control valve is associated with the cryogen supply line for controlling cryogen flow. An operator interface is operatively connected to the cryogen supply line for selectively regulating cryogen fluid flow from the cryogen fluid source through the cryogen supply line. A computing device is provided for controlling or monitoring device operating parameters. The computing device including a user-perceptible display and at least one user-manipulable control. A connection is provided for supplying cryogen from the cryogen feed line to an umbilical.

BRIEF DESCRIPTION OF THE DRAWINGS

For a better understanding, reference may be made to the accompanying drawings, in which:

FIG. 1B is a schematic side view of a component of the aspect of the invention of FIG. 1A;

Figure 1A:
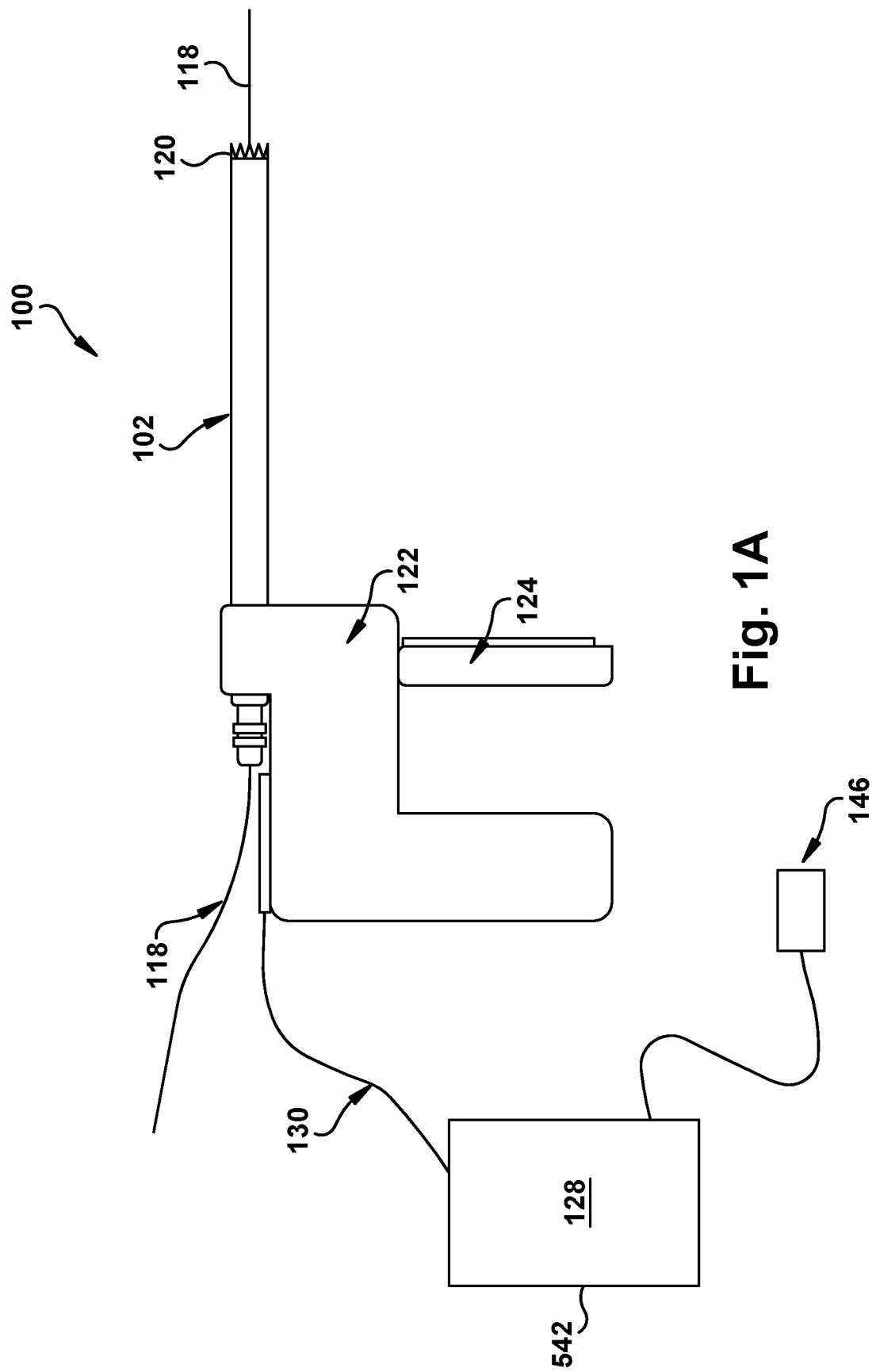
FIG. 1A is a schematic side view of an aspect of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DESCRIPTION OF ASPECTS OF THE DISCLOSURE

Unless defined otherwise, all technical and scientific terms used herein have the same meaning as is commonly understood by one of skill in the art to which the present disclosure pertains.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

The invention comprises, consists of, or consists essentially of the following features, in any combination.

The system, device, and console disclosed herein facilitate removal of leads such as, e.g., those of a cardiac pacemaker. The integration of freezing into conventional cardiac lead extraction methods increases tissue rigidity, thereby improving ability to cut through tissue, such as scar tissue, at sites where the leads have become affixed to the vasculature. Freezing tissue to warm subfreezing temperatures (e.g., greater than −20° C., greater than −25° C., or greater than −30° C.) reduces lead extraction time. The targeted application of sub-lethal freezing of tissue in which a lead is embedded just distal to the cardiac pacemaker lead extractor while minimizing/not freezing the blood vessel wall may be desirable for procedural success. For example, application of liquid carbon dioxide ($liCO_2$) as the cryogen source provides the freezing temperatures necessary to attain cryo-fixation at the target tissue site in less than 10 seconds. The use of low pressure $liCO_2$ also does not require a high pressure Joule-Thompson based cryogen gas cooling system, and provides for a patient-friendly environment.

A cryoconsole or cryo-fixation lead extraction system as disclosed herein may be used in connection with any of the various cryo-fixation device implementations also disclosed herein, or other commercially available lead extraction devices available. Further, the lead extraction devices disclosed herein may be used in connection with the cryoconsole disclosed herein or with other commercially available consoles for controlling and/or monitoring cryogenic devices and/or lead extraction devices.

At least one implementation of the present invention is described below in reference to its application in connection with a system, device, and cryoconsole for use in cryo-fixation for cardiac pacemaker lead extraction. At least one implementation of the present invention is described below in reference to a nominal size and including a set of nominal dimensions. However, it should be apparent to those skilled in the art that the present invention is likewise applicable to any suitable lead extraction device and console device, including for extraction of leads associated with other surgically implanted cardiac devices, e.g., leads for use with implantable cardioverter defibrillators. Further, it should be apparent to those skilled in the art that the present invention is likewise applicable to various scales of the nominal size and/or nominal dimensions.

Cryo-Fixation Extractor Device

A number of implementations of a cryo-fixation cardiac pacemaker lead extraction device are disclosed herein.

Open Loop Devices

In one example implementation, the cryo-fixation cardiac pacemaker lead extraction device may include a lead extraction catheter, and a liner disposed along the lead extractor catheter and within a lumen therein. At least one cryogen supply line may be provided within the liner. For example, and as shown in certain of the Figures, two cryogen supply lines may be provided. Each of the one or more cryogen supply lines may terminate at a cryogen spray nozzle, near the catheter/cutting member interface or the cutting member/tissue interface.

The supply lines and nozzles may be configured to spray liquid cryogen onto a target tissue from a location near the cutting member located at the distal tip of the cardiac pacemaker lead extractor device. The target tissue may be, e.g., scar tissue in which the lead tip is embedded. Upon application, e.g. spraying, of liquid cryogen onto the target tissue, the cutting member may cut through the tissue to break up the scar tissue and release the lead tip more readily than if the target tissue were at body temperature.

The liner may be free floating in the lumen of the extractor catheter to enable rotation of the extractor (facilitating use of the cutting member) while providing an anchor point for the cryospray supply lines. Alternatively, the liner may be integrated into the cavity of the extractor device's lead extraction channel, which is affixed to the extractor device handle at the distal end (not pictured). In either of these cases, the liner may be made of, e.g., polymer, nylon, polyamide, or similar material. As an example, the liner dimensions may be, e.g., about 11 French (Fr) (0.139" OD, ID 0.129", wall 0.005"), allowing the liner to run the entire length of the extraction catheter (0.152" ID), ending at the distal end within the cutting member tip (0.142" ID). The cutting member tip inner dimension (ID: 0.142") may be the rate limiting dimension for the max outer dimension (OD) of the liner.

In various configurations, one, two, or more than two cryogen spray supply lines may be provided on the inner lumen of the liner to enable delivery of the cryogen to the distal end of the extraction catheter. For example, as shown in certain of the Figures, two such supply lines are depicted in cross section. As noted, these supply lines run the entire axial length of the liner, and may be affixed to the inner lumen of the liner. The supply lines may have dimensions of, e.g., 23 or 25 gauge (0.02" to 0.025" OD) within the liner, and may be, for example, stainless steel hypotubing or similar polymer based tubing. At the proximal end of the extractor device supply lines, they may be affixed to the extractor handle. At the extractor handle, the extractor device supply lines may be coupled to, or transition to an umbilical for connection to the cryogen supply console.

In some implementations, the liner may be used in connection with a conventional commercially available lead extractor device, such as a COOK lead extractor (available from Cook Inc. of Bloomington, Indiana), or any other desired lead extractor. In such an implementation, the liner may provide a retrofit so that a commercially available lead extractor device may be used in connection with open loop cryo-fixation to enhance the lead removal process. In other implementations, a cardiac pacemaker lead extractor device may include the liner, either as an integrated feature or as a removable member.

Closed Loop Devices

Other implementations of cardiac pacemaker lead extractor devices and liners are disclosed herein, which provide a closed loop cryo-fixation system. Similar to the open loop cryo-fixation device described above, closed loop implementations may include a lead extraction catheter, and a liner disposed along the lead extractor catheter. At least one cryogen supply line may be provided within the liner. The cryogen supply line(s) provide cryogen to a distal cooling chamber located at the distal tip of the liner. The distal cooling chamber acts in operation as a freeze applicator tip, and may be substantially annularly (i.e., ring or donut) shaped, so that the lead to be removed may pass through a hole in the center of the chamber. The distal cooling chamber may be disposed near the catheter/cutting member interface or the cutting member/tissue interface. The lead extraction device may further include at least one cryogen return line disposed within the liner, for transmitting used cryogen from the distal cooling chamber toward the proximal end of the device for recovery. The cryogen supply line(s) may be substantially similar to those previously described with respect to open loop implementations. The return line(s) may be similar in dimensions to the supply line, or may be larger in diameter. The return lines may run parallel or concentric to the supply lines within the liner.

Closed Loop—Internal Liner

In one closed loop implementation, the liner may be disposed within an internal lumen of the lead extraction catheter, similar to the manner described above and depicted in certain of the Figures. However, in addition to the at least one cryogen supply line, at least one cryogen return line may also be disposed within the liner. The supply line(s) may be configured to receive liquid or gaseous cryogen and transmit the cryogen to the cooling chamber at the distal tip of the device, and the return lines may be configured to carry used cryogen away from the distal tip for recovery.

Closed Loop—External Liner

In another closed loop implementation, the liner may be disposed circumferentially around the outside surface of the lead extraction catheter in a sleevelike fashion. The at least one cryogen supply line and at least one cryogen return line may be disposed within the liner, around the outer surface of the lead extraction catheter, and may be configured to receive liquid or gaseous cryogen and transmit the cryogen to the cooling chamber at the distal tip of the device.

The liners described with respect to the closed loop—internal liner implementation and the closed loop—external liner implementation may be used in connection with a conventional commercially available lead extractor device, such as a COOK lead extractor (available from Cook Inc. of Bloomington, Indiana), or any other desired lead extractor. In such implementations, the liner may provide a retrofit so that a commercially available lead extractor device may be used in connection with closed loop cryo-fixation to enhance the lead removal process. In other implementations, a lead extractor device may be provided including the liner, e.g., as a removable member.

Closed Loop—Integrated

In another implementation, the lead extraction device may include a lead extraction catheter similar to that used in the closed loop—internal liner implementation. However, unlike the internal liner implementation, the integrated implementation may include at least one cryogen supply line, at least one cryogen return line, and the distal cooling chamber integrated directly into the lead extraction device, in lieu of a liner. In such an implementation, the cooling chamber may be disposed at the distal tip of the extraction catheter shaft, and may include a cutting member on its distal end.

As in open loop implementations, the supply lines present in any of the foregoing closed loop devices may be affixed to the extractor handle at the proximal end of the supply line(s). At the extractor handle, the extractor device supply lines may be coupled to, or transition to an umbilical for connection to the cryogen supply console.

The umbilical may be a lightweight tube, configured to house umbilical cryogen supply lines to fluidly connect the proximal end of the extractor device supply lines with the cryoconsole. The umbilical may include a supply line or lines disposed therein and which run the length of the umbilical. The supply lines may have dimensions of, for example, about 19 gauge (0.042" OD). The umbilical may be made of stainless steel hypotubing or similar polymer based tubing, and may be about 6 to 10 feet in length, although other lengths are clearly contemplated.

A connection may be provided, for connecting or coupling the umbilical supply line to the cryoconsole. The connector may use a twist, threaded, or other attachment mechanism to couple the umbilical supply line to the cryoconsole. Some implementations may use a single connection point, while others may use separate connection points for cryogen and electrical components. Additionally, separate connectors may be provided for coupling the return lines to the cryoconsole in an analogous fashion.

Regardless of the implementation selected from the foregoing, any combination of features disclosed above, or any arrangement that is functionally equivalent thereto, the cryofixation cardiac pacemaker lead extractor device may be configured to be utilized with any number of cryogens including, for example, various forms of nitrogen, argon, carbon dioxide, nitrous oxide, and others, as will be appreciated by the skilled artisan. Further, the cryogens may be provided at a wide range of input pressures, for example, from about 22 psi to about 6,000 psi.

Cryoconsole

The cryoconsole may configured to provide controlled delivery of cryogen to any configuration of cryoprobe (probe, needle, catheter, etc.) used to freeze targeted tissue including a cardiac pacemaker lead extractor device such as, e.g., the device shown and described herein. The cryogen may be delivered at any desired pressure, preferably the lowest pressure that is capable of delivering the cryogen to the distal freeze tip of a cryoprobe such as the cardiac pacemaker lead extraction device, i.e., either the cryogen spray nozzle(s) or the distal cooling chamber. The cryogen may be, e.g., carbon dioxide in liquid ($liCO_2$) or gas ($gCO_2$) form, nitrogen, nitrous oxide, or other cryogens as will be appreciated by one of ordinary skill in the art and as noted herein.

A cryoconsole device may include cryogen plumbing features including a cryogen source, e.g., a pressurized cryogen cylinder; a pressure regulator; a pressure transducer; an electronic controlled solenoid; and other features as will be appreciated by one of ordinary skill in the art.

An onboard control system computing device may be used to control operating parameters, and may further include a peripheral interface providing digital and/or analog inputs and outputs (e.g., LABJACK, a registered trademark of LabJack Corp. of Lakewood, Colorado), electronic controller, PC-based controller interface, and optional remote cryogen activation foot pedal control. User interface features may include controls for regulating freeze time, monitor cryogen tank pressure level, freeze on/off indicator, and a freeze on/off activation control, e.g., a button.

In some implementations, the cryoconsole may be in the form of a portable console. In an implementation, the console may be mounted on a mounting pole in a configuration similar to, e.g., an IV pole, and may include a base with casters mounted thereon. The cryogen tank may be removably affixed to the mounting pole. A cryogen pressure regulator may be associated with the cryogen tank or with the cryogen feed line to regulate cryogen pressure to a cryoprobe attached to the cryoconsole. A cryogen feed line may be provided for carrying liquid and/or gaseous cryogen from the cryogen tank to a cryoprobe attached to a cryoprobe connector on cryoconsole device. A cryogen flow control valve is associated with the cryogen feed line to control cryogen flow from the cryogen tank through the cryogen feed line and to the cryoprobe. The cryoprobe is connected to the cryogen feed line within the cryoconsole via a cryoprobe connector located on the cryoconsole wherein the umbilical of a cryoprobe is connected to said cryoprobe connector. An additional connection point may be provided for a foot pedal, the foot pedal being operatively connected to the cryoconsole to control cryogen flow (on/off) through the cryogen feed line. Some implementations may include such a foot pedal, hand trigger, key pad or other remote controller coupled to the cryoconsole to control cryogen flow to the attached cryoprobe.

A computing device may be provided for controlling and monitoring operating parameters of the cryoconsole during operation. The computing device may further include a display and a control panel. A connection or connections may additionally be provided for supplying cryogen from the cryogen feed line to a cryoprobe via the cryoprobe umbilical, and for recovering cryogen from the cryogen return line within the umbilical and back to the cryoconsole.

Ex Vivo Testing

An ex vivo testing model may be used to establish cryogen application pressure and time guidance parameters. One such model may include directed application of cryogen spray on the surface of porcine muscle tissue at 37° C. (±10%). Tissue temperature may be measured via remote sensing, with target tissue temperature between −10° C. and −20° C. The remote sensing point may be, e.g., near catheter/tissue interface at about 1-2 mm under the tissue surface. Temperatures may be recorded at intervals of, e.g., 1 second during the freeze interval.

A target cryospray application pressure may be, e.g., less than 150 psi for $liCO_2$, or less than 800 psi for $gCO_2$. An example initial target application pressure may be, e.g., 25 psi for $liCO_2$, with upward adjustments at intervals of, e.g., 25 psi, until target temperature range is reached. Target temperature range may be reached in, e.g., 10 seconds. Alternatively, $gCO_2$ may be provided at a pressure of about 800 psi, and then reduced by, e.g., 200 psi until target temperature range is no longer attained within, e.g., 10 seconds. A target application time may be, e.g., 10 seconds or less, and preferably as short as possible. An initial application time may be, e.g., 10 seconds, but may be modified in, e.g., 5 second intervals as needed to attain the desired tissue temperature in a given application.

A modified heat loaded porcine tissue model may be used to evaluate an optimal time and pressure settings range under a heat loaded model. In this model, an approximately 5 Fr model wire bundle may be inserted below the surface of a section of porcine muscle at several points along the tissue. The bundle may be imbedded about 1-2 mm below the tissue surface for a distance of about 5 mm. The tissue model may be placed in a 37° C. (±10%) circulating bath of liquid media to simulate heat load from blood flow. Tissue temperature monitoring may include the following parameters: target tissue temperature between −10° C. and −20° C., remote sensing point near catheter/tissue interface, and approximately 1 sec recording intervals during freeze interval.

In summary, a cold-tip powered cardiac pacemaker lead extraction device is disclosed herein to cool the fibrous tissue surrounding the cardiac lead and, optionally, engage the tissue as desired with a rotating and/or oscillating cutting blade. By delivering cool energy, the lead extraction device can help to fix or stabilize the tissue, facilitating more precise cutting. A trigger-actuating mechanism may be used to cut through cooled tissue, but it is also contemplated that an automated turning mechanism may be used to facilitate faster rotation, or vibration or oscillation may be used to help cut through the cooled tissue to free the embedded lead.

Additionally, the lead extraction device could include internal and/or external thermocouples or temperature sensors to monitor temperatures within the tissue and/or help control appropriate delivery of thermal energy.

A detailed description of an example cryo-fixation cardiac pacemaker lead extraction device according to the above disclosure will be given below, with reference to the Figures. Similar element names are used below to reference analogous structures described above. FIGS. 1A-1B depict a cryo-fixation lead extraction device 100 comprising a lead extraction catheter 102 having longitudinally spaced proximal and distal catheter ends 104 and 106, respectively, and an elongate catheter lumen 108. The longitudinal direction, as used herein, is substantially horizontal in the orientation of FIG. 1B and is represented by arrow L.

With particular reference to FIG. 1B, the cryo-fixation lead extraction device 100 includes a liner 110 having longitudinally spaced proximal and distal liner ends 112 and 114, respectively, and an elongate liner lumen 116. The liner lumen 116 is configured to selectively accept at least part of a lead 118 (which is being extracted) longitudinally therethrough. (The lead 118 being extracted is shown in FIG. 1A as extending through an entirety of the liner 110 and lead extraction catheter 102, and through a portion of a handle 120 device.) The lead 118 being extracted will be shown and described herein as a cardiac pacemaker lead, though it is contemplated that the lead extraction device 100 could be used to help remove any suitable elongate structure, particularly one that has become embedded or ingrown, from a patient's bodily tissue.

At least a portion of the liner 110 is located a chosen one of circumferentially within and circumferentially surrounding the catheter lumen 108, i.e., at least a portion of the liner 110 is located either circumferentially within or circumferentially surrounding the catheter lumen 108. The term "circumferential" is used herein to reference a direction in a plane which is substantially perpendicular to the longitudinal direction and is taken with respect to a centerline of at least one of the liner 110 and the catheter lumen 108. In other words, the liner 110 may be at least partially inserted into the lead extraction catheter 102 or vice versa, and one of ordinary skill in the art will be able to configure a suitable arrangement for a desired use environment. In FIG. 1B, the liner 110 is shown as being located within the catheter lumen 108. The liner 110 may be flush, recessed slightly into, or protruding slightly from either or both ends of the catheter lumen 108, but one of ordinary skill in the art will be able to configure a cryo-fixation lead extraction device 100 as desired for a particular use environment. For example, the distal end of the liner 110 and distal cooling chamber 432 may terminate at the distal end of the catheter 106 just proximal to or flush with the cutting surface of the cutting feature 120, when present, to facilitate cutting by the cutting feature 120.

The liner 110 may be configured for rotational movement (i.e., movement around a longitudinal axis) with respect to the catheter lumen 108. This may be particularly useful, for example, when at least one of the lead extraction catheter 102 and the liner 110 includes a cutting feature 120 located adjacent the distal catheter end 106 (e.g., carried on, or comprising, one or both of the distal catheter end 106 and the distal liner end 114). In some embodiments, the cutting feature 120 may be located on the distal catheter end 106 or the distal liner end 114, with the lead extraction catheter 102 being configured for oscillational motion relative to the liner 110 and rotational motion about a longitudinal axis relative to the liner 110. For example, the liner 110 may remain in a fixed position and the catheter 102 rotates about the liner 110 during the cutting action, or vice versa.

When present, the cutting feature 120 may be configured to selectively mechanically cut into at least a portion of the patient tissue cooled zone Z (shown in FIGS. 6-7) adjacent the lead 118 being extracted. The term "mechanically cut" is used herein to indicate that the patient tissue is severed via direct contact with at least one edged structure that is sufficiently sharp to disrupt, tear, cleave, or break the patient tissue via mechanical force. "Mechanical cutting" is intended to differentiate from the use of an electrically edged structure such as a Bovie knife or a laser. For example, and as shown in FIG. 1A, the cutting feature 120 may be a serration 124 located at the distal catheter end 106. When the lead extraction catheter 102 and liner 110 are configured for rotational motion relative to each other, one of these structures can be held relatively stationary within the patient tissue while the other one rotates and/or oscillates to help actuate the cutting feature 120 (e.g., "scoop" or "cookie cut" the tissue with the serration 124). It is also contemplated that both the distal catheter end 106 and the distal liner end 114 may include an edge portion (not shown) which can collectively act in a scissors-type action under relative rotational and/or longitudinal motion to mechanically cut the patient tissue.

When the lead extraction catheter 102 is carried by a handle 122 as shown in FIG. 1A, a trigger 124 or other user-manipulable control may be provided (and powered appropriately) to selectively actuate the relative rotation between the liner 110 and the lead extraction catheter 102, regardless of which of these structures is stationary in an absolute frame of reference.

At least one cryogen supply line 126 (two shown in FIG. 1B) extends longitudinally through at least a portion of the liner lumen 116. The at least one cryogen supply line 126 may be affixed to an inner surface of the liner lumen 116. The cryogen supply line 126 is configured to place a cryogen fluid source 128 (which is located in operative proximity to the proximal liner end 112) into fluid communication with the distal liner end 114. The cryogen supply line 126 is configured to selectively generate a patient tissue cooled zone adjacent the distal catheter end 106, upon operation.

Figure 2:
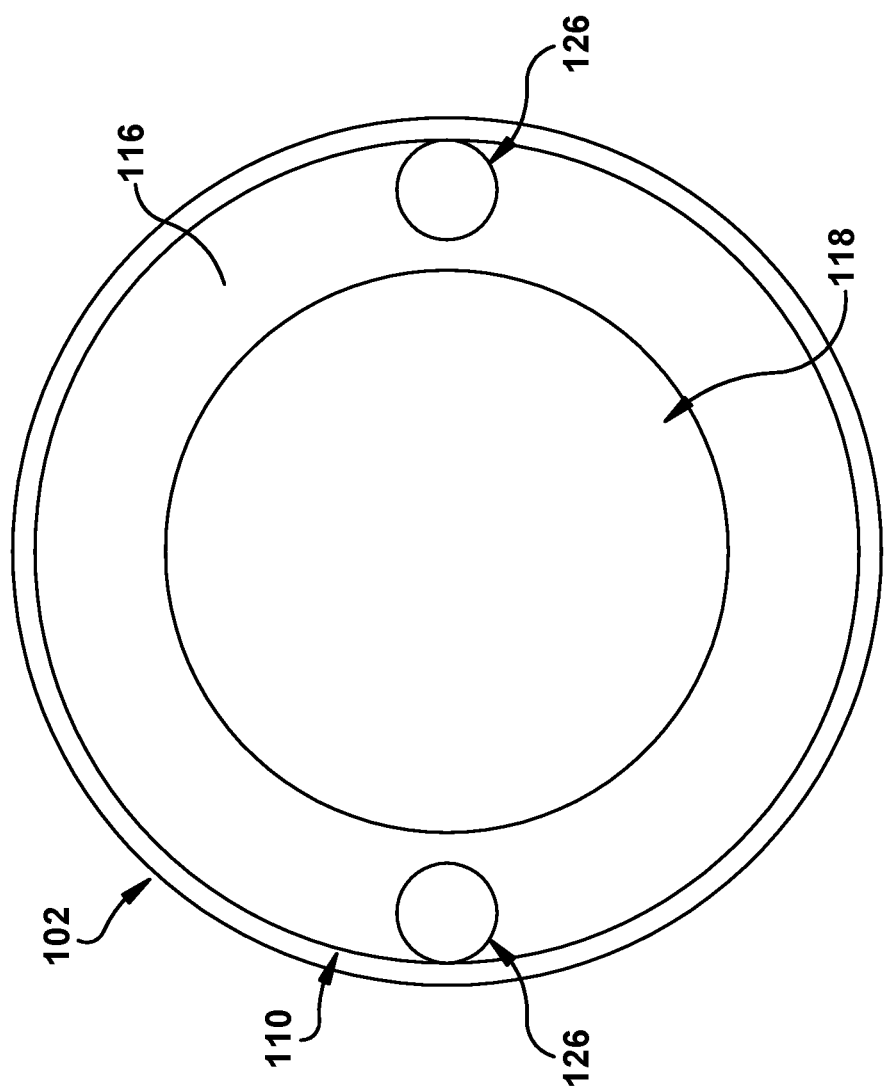
FIG. 2 is a cross sectional view of a component of the aspect of FIG. 1A in a first configuration.
Figure 3:
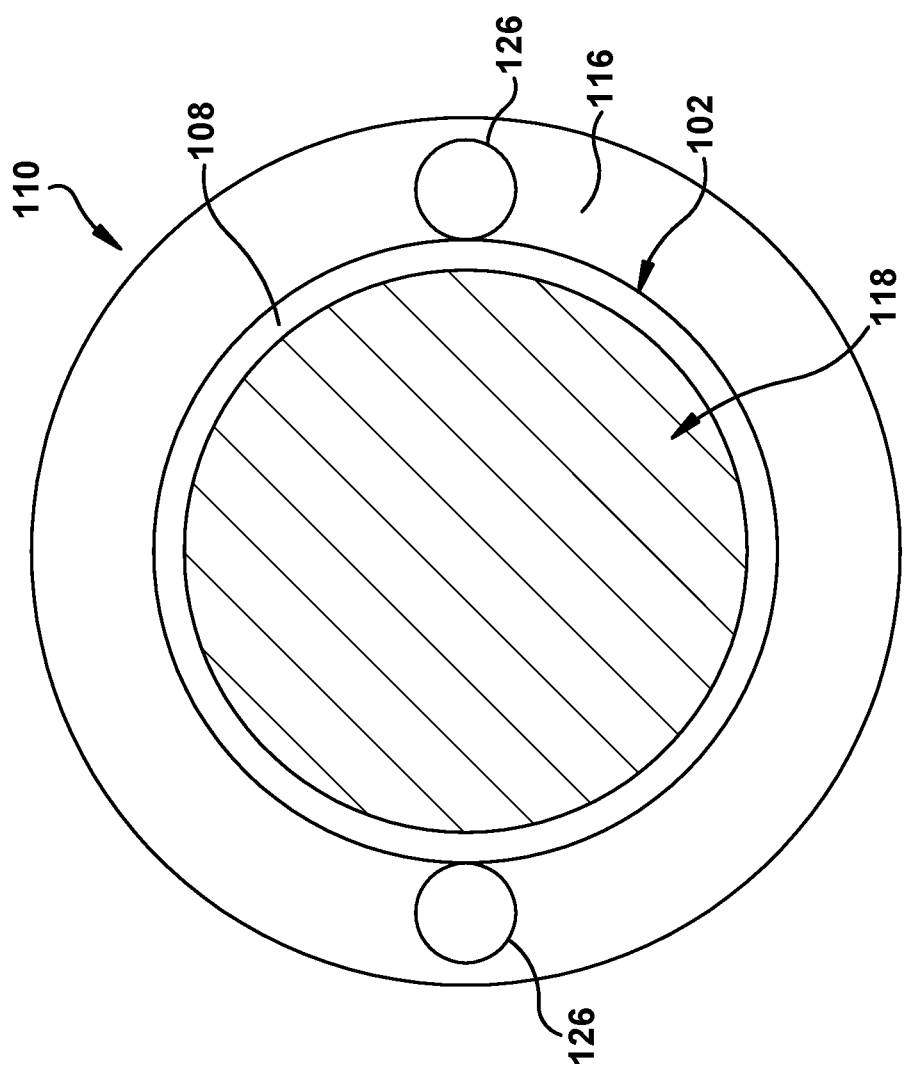
FIG. 3 is a cross sectional view of a component of the aspect of FIG. 1A in a second configuration.

With reference now to the cross-sectional views (viewed from a direction parallel to the longitudinal direction) of FIGS. 2-3, two example configurations of components of the cryo-fixation cardiac pacemaker lead extraction device 100 are shown. These correspond to the internal liner and external liner versions of the open loop device described above. In FIG. 2, the liner 110 is located inside the catheter lumen 108, with the cryogen supply lines 126 located inside the liner lumen 116 and adjacent to the lead 118 being extracted, which is also located inside the liner lumen 116 (and spaced apart from the lead extraction catheter 102 by the liner 110). In FIG. 3, the lead extraction catheter 102 is located inside the liner lumen 116, with the cryogen supply lines 126 located inside the liner lumen 116 and outside the lead extraction catheter 102. The lead 118 being extracted is located inside the catheter lumen 108 (and spaced apart from the liner 110 and the cryogen supply lines 126 by the lead extraction catheter 102).

Figure 4B:
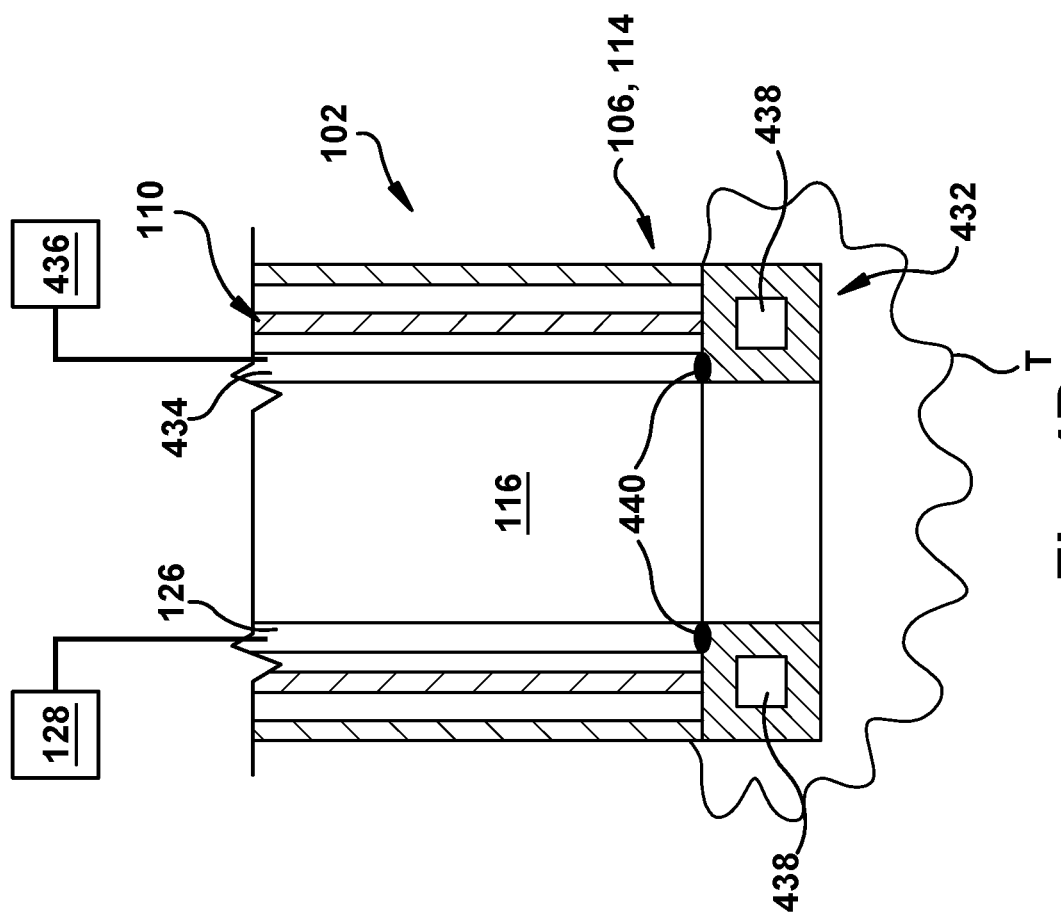
FIG. 4B is a cross sectional view of the component of FIG. 3 in the second configuration during operation.
Figure 4A:
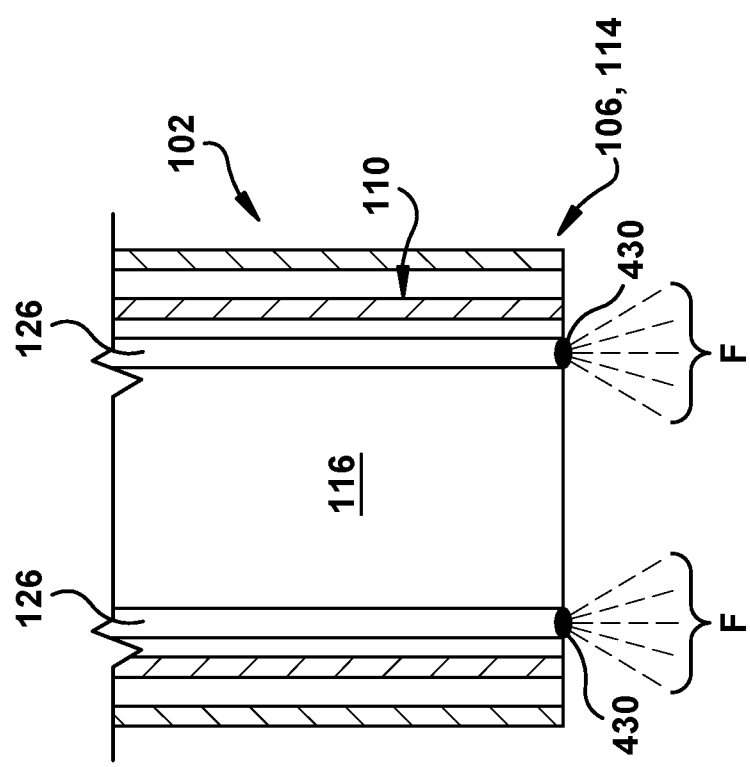
FIG. 4A is a cross sectional view of the component of FIG. 2 in the first configuration during operation.

FIGS. 4A and 4B depict cross-sectional views (viewed from a direction perpendicular to the longitudinal direction) of two example configurations of components of the cryo-fixation lead extraction device 100, each of which could be used with either or both of the example configurations of FIGS. 2-3.

In FIG. 4A, which is analogous to the open loop system described above, at least one cryogen supply line 126 (two shown) sprays cryogen fluid F through a nozzle 430 (here, one nozzle 430 is shown for each cryogen supply line 126) and toward an ambient patient tissue adjacent the distal catheter end 106. FIG. 4B, in contrast, shows a system analogous to the closed loop system described above.

In FIG. 4B, a distal cooling chamber 432 is located adjacent the distal liner end 110 and is in fluid communication with the cryogen fluid source 128 (shown schematically in FIG. 4B) via at least one cryogen supply line 126. The distal cooling chamber 432 can form a part of, and/or be attached to, either or both of the lead extraction catheter 102 and the liner 110. At least one cryogen return line 434 extends longitudinally through at least a portion of the liner lumen 116. The cryogen return line 434 is configured to place the distal cooling chamber 432 in fluid communication with a cryogen fluid destination (shown schematically in FIG. 4B at 436) via the proximal liner end 112. The cryogen fluid source 128, the cryogen supply line 126, the distal cooling chamber 432, the cryogen return line 434, and the cryogen fluid destination 436 collectively comprise a closed cryogen loop preventing passage of cryogen fluid F distally from the cryo-fixation lead extraction device 100.

The liner 110 in the configuration of FIG. 4B may at least partially circumferentially surround the lead extraction catheter 102, with the cryogen supply line 126 and the cryogen return line 434 at least partially interposed radially between the liner 110 and the lead extraction catheter 102. The lead extraction catheter 102 may instead at least partially circumferentially surround the liner 110, with the cryogen supply line 126 and the cryogen return line 434 at least partially interposed radially between the lead extraction catheter 102 and the liner 110. The supply line 126 and return line 434 may also be disposed within the lead extraction catheter 102 wall. In this configuration, the cardiac pacemaker lead extraction catheter 102 and liner 110 will be integrally formed as a single tube.

The distal cooling chamber 432 may have any desired configuration. For example, the distal cooling chamber 432 is shown in FIG. 4B as being a hollow annular structure, with the cryogen supply and return lines 126 and 434 being placed in fluid communication with an interior 438 of the distal cooling chamber 432 via fluid interfaces 440, to assist in circulating cryogen fluid through the distal cooling chamber 432 in a closed-loop system. The distal cooling chamber 432 is configured to exert a thermal energy field T (without emission of cryogen fluid) upon the ambient patient tissue adjacent the distal catheter end 106.

Figure 5:
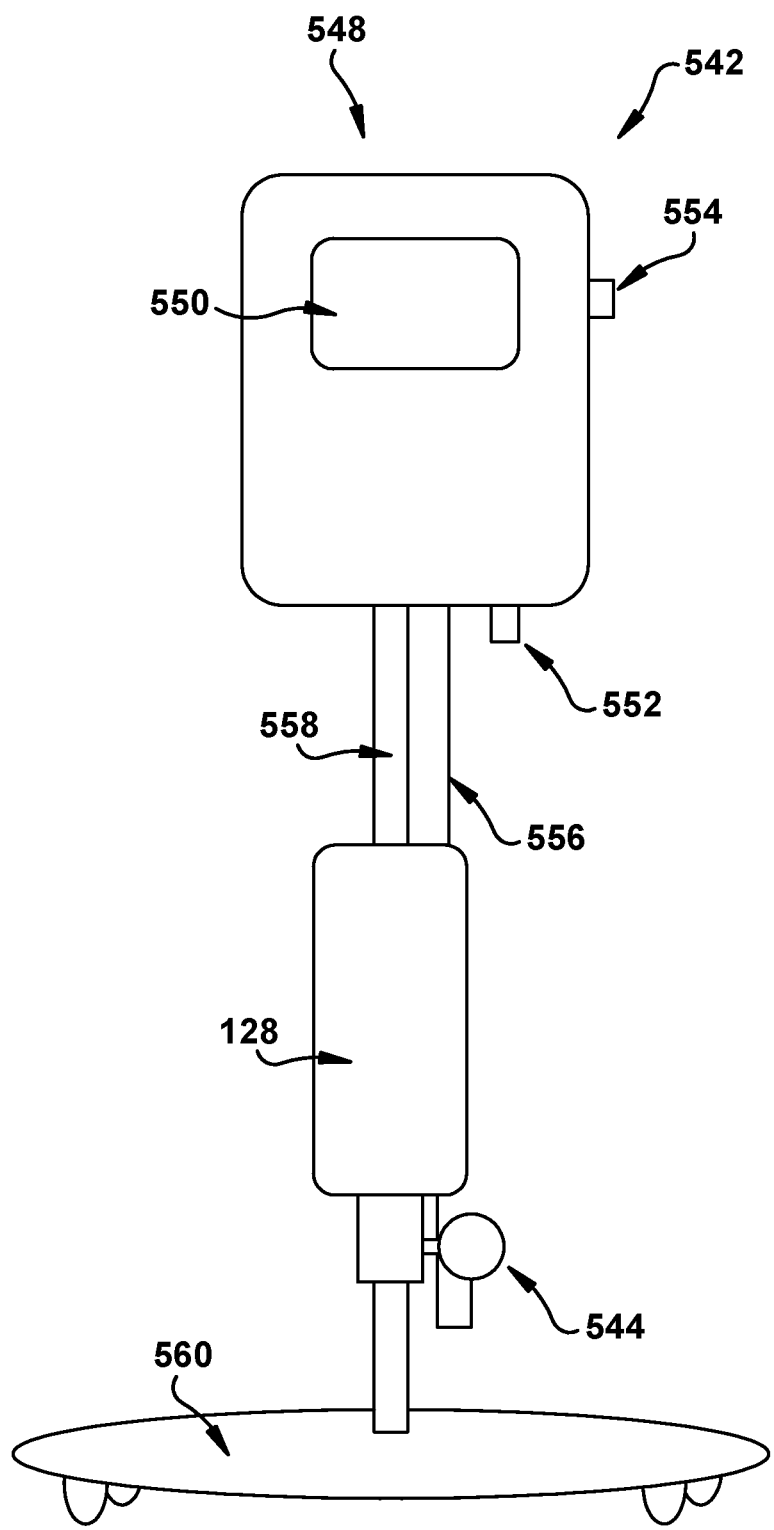
FIG. 5 is a schematic depiction of an example component of a system including the aspect of FIG. 1A.

FIG. 5 depicts a cryoconsole 542 which can be used with any cryoprobe. The cryoconsole 452 may be utilized along with the cryo-fixation cardiac pacemaker lead extraction device 100 shown in the other Figures, to comprise a cryo-fixation lead extraction system, along with any desired cryogen plumbing features. The cryoconsole 542 may be compatible with any number of configurations of probes and devices when attached to the cryoconsole via the cryoprobe connector 554. A cryogen fluid source 128 and the cryo-fixation lead extraction device 100 are provided. A cryogen regulator 544 is associated with the cryogen fluid source 128 or cryogen supply line 126. An operator interface 146, shown schematically in FIG. 1, (which may be operatively connected to or contained within the cryoconsole 542) is operatively connected to a cryogen flow control valve within or attached to the cryogen supply line 126 for selectively regulating cryogen fluid flow. The operator interface 146 may be of any desired type such as, but not limited to, a foot pedal, hand-operated switch, voice-operated switch, or any other suitable operator interface 146. It is also contemplated that the cryo-fixation lead extraction device 100 could include an onboard supply of cryogen fluid, in addition to or instead of the described separate cryogen fluid source 128 attached via cryogen supply line 126.

A computing device 548 within or otherwise associated with the cryoconsole 542 is provided for at least one of controlling and monitoring cryogen pressure, flow, temperature, on/off status, among other operating parameters. The computing device 548 may also provide for at least one of controlling and monitoring the cryo-fixation cardiac pacemaker lead extraction device 100 or other cryoprobe during operation, the computing device 548 includes a user-perceptible display 550 and at least one user-manipulable control, which may include a touch-sensitive portion of the user-perceptible display 550, the operator interface 146, a power switch, a lockout key, or any other desired user-manipulable control. The operator interface 146 may be operatively connected to the computing device 548 via interface connector 552 or integrated into the display 550. The cryogen supply line 126 within a cryoprobe, such as the cardiac pacemaker lead extraction device 100, may be operatively connected to the cryogen fluid source 128 via an umbilical 130 attached to the cryoprobe connector 554 on the cryoconsole 542, and then feed line 556 to the cryogen fluid source 128, wherein the cryogen flow may be controlled via a pressure regulator 554 or other control valve and monitored and controlled by the computing device 548 to assist with regulating cryogen fluid flow.

When the cryo-fixation lead extraction device 100 is of the closed-loop type, then the system will include a cryogen fluid destination 436, with the cryoconsole 542 being operatively connected to at least one of the at least one cryogen return line 434 and the cryogen fluid destination 436 via an umbilical 130 attached to the cryoconsole 542 at the cryoprobe connector 554 for selectively regulating cryogen fluid flow. For example, the cryogen return line 434 could be connected to the cryogen fluid destination 436 via the connector 554 on the cryoconsole 542, wherein the cryogen flow may be monitored or controlled by the computing device 548 and/or operator interface 146 to assist with regulating cryogen fluid flow.

The computing device 548 may include any suitable bespoke or standardized treatment assistance programming for controlling and/or monitoring cryogen flow to and from the cryoconsole 542 including to the cryo-fixation lead extraction device 100 or other probe or device when affixed to the cryoconsole 542 via the cryoprobe connector 554 as desired. The treatment assistance programming can readily be provided by one of ordinary skill in the art for a particular use environment.

The cryoconsole 542 may include a portable mounting frame (e.g., mounting pole 558 and castered base 560) which is configured to support and transport at least the cryogen fluid source 128, cryogen regulator 544, operator interface 146, and computing device 548, to allow a cryoprobe, such as the cryo-fixation lead extraction device 100, to be used in many different settings and circumstances within a facility and to be easily moved between, for example, operating rooms or catheter labs.

Figure 6:
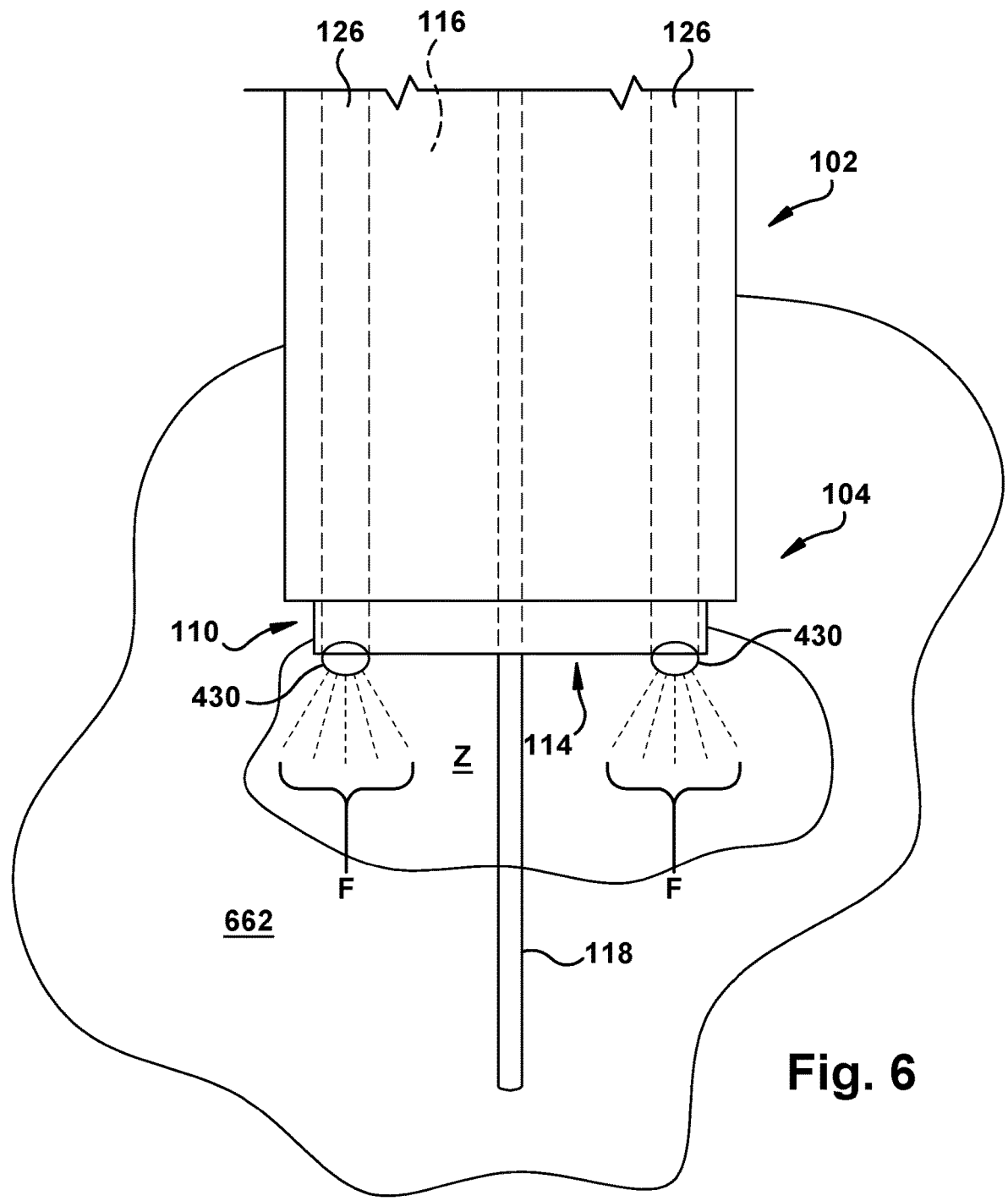
FIG. 6 is a schematic partial side view of the component of FIG. 2 in the first configuration during operation in an example use environment.
Figure 7:
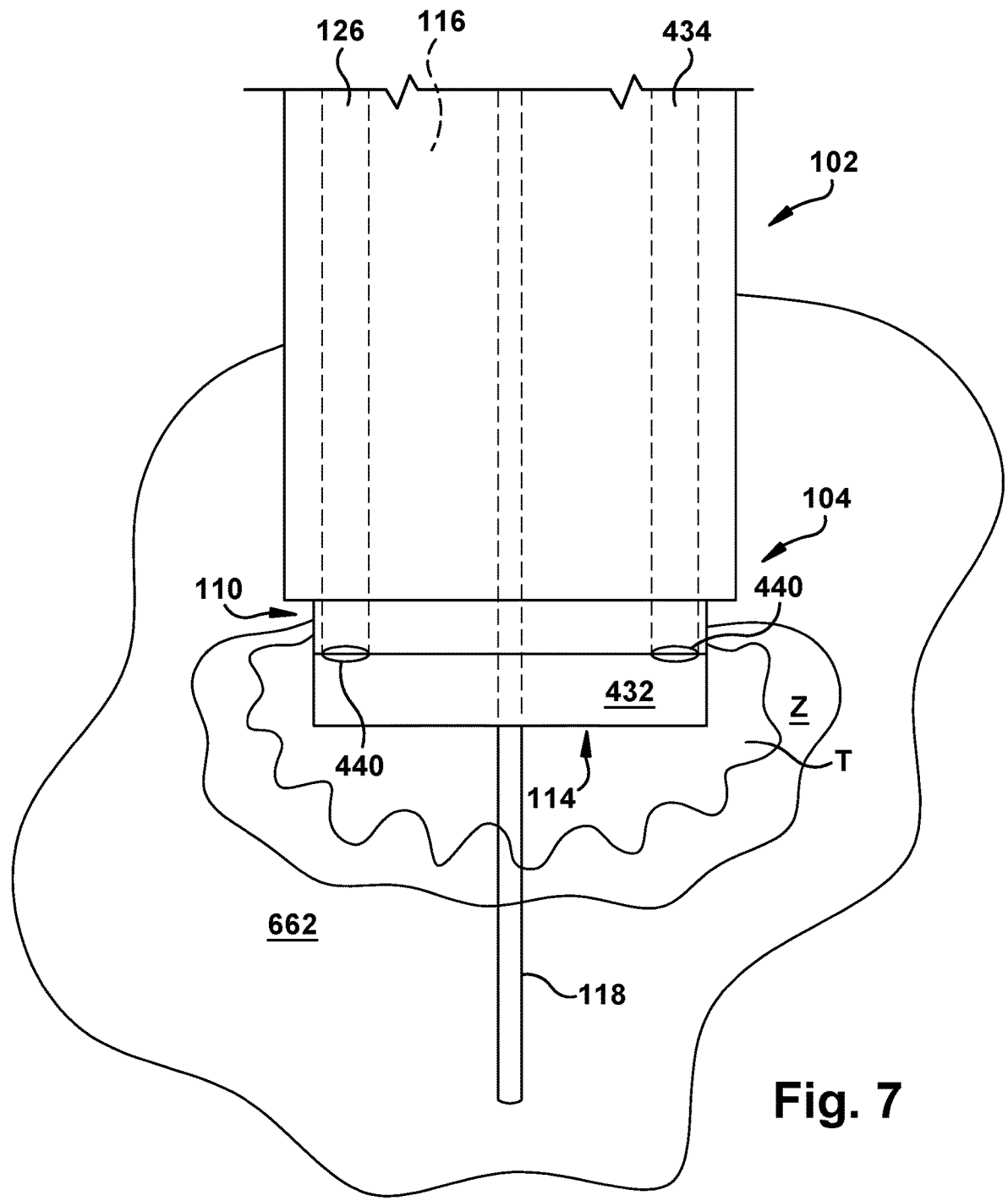
FIG. 7 is a schematic partial side view of the component of FIG. 3 in the second configuration during operation in an example use environment.

FIGS. 6 and 7 schematically depict variations on a method of extracting a lead 118 from a patient tissue 662 volume. FIG. 6 depicts the use of the open-loop system of FIG. 4A, and FIG. 7 depicts the use of the closed-loop system of FIG. 4B. In both cases, first, the cryo-fixation lead extraction device 100 is provided. With the cryogen supply line 126, a cryogen fluid source 128, which is in operative proximity to the proximal liner end 112, is placed into fluid communication with the distal liner end 114. At least part of the lead 118 being extracted is extended longitudinally into or through the liner lumen 116. Cryogen fluid F from the cryogen fluid source 128 is selectively directed through the cryogen supply line 126 to selectively generate a patient tissue cooled zone Z adjacent the distal catheter end 106 within the patient tissue 662 volume. For the open-loop system of FIG. 4A, this is done via spraying of the cryogenic fluid F through the nozzle(s) 430. In the closed-loop system of FIG. 4B, this is done via circulation of the cryogenic fluid F through the closed cryogenic loop and application of the thermal energy field T to the patient tissue 662 volume.

Within the patient tissue cooled zone Z, the lead 118 is loosened from the patient tissue 662. This can be done via vibration (manually or automatically applied), the user's wiggling or shaking the lead 118, or in any other desired manner. In some use environments, loosening the lead 118 from the patient tissue 662 will include selectively mechanically cutting into at least a portion of the patient tissue cooled zone Z adjacent the lead 118 being extracted—for example, through use of a cutting feature 120 of any desired type. The loosened lead 118 is then moved proximally with respect to the liner lumen 116 such as, for example, by being pulled deeper into the liner lumen 116 and/or by the lead extraction catheter 102 and other structures of the cryo-fixation lead extraction device 100 being pushed further into the patient tissue 662. This freezing and loosening cycle is repeated until the entire lead 118 has been released, and optionally accepted into the liner lumen 116, and the cryo-fixation lead extraction device 100 is then removed from the patient tissue.

As desired, and particularly when not enough of the lead 118 being extracted is available for the user to readily pull or tug upon during the extraction process or when the user is concerned about fragility or breakage of the lead 118 being extracted, a stylet may be passed longitudinally into the liner lumen 116. The stylet can then be secured to the lead 118 being extracted; and proximally directed longitudinal force exerted on the stylet to assist with moving the loosened lead 118 proximally with respect to the liner lumen 116.

As is clear from the foregoing disclosure, aspects of the invention provide a number of different devices which may be used independently of one another or in combination with a cryo-fixation system. For example, the following are all contemplated and considered part of the invention:

Point 1—A cryo-fixation liner as described herein, configured to be peripherally disposed on the interior or the exterior of a lead extraction catheter, which may be a conventional and/or commercially available lead extraction catheter, wherein the cryo-fixation liner includes a supply line providing liquid or gaseous cryogen to a distal tip of the lead extraction catheter.

Point 2—The cryo-fixation liner of point 1, wherein the cryo-fixation liner is configured to fit over a circumferential outer surface of the lead extraction catheter in a sleeve-like fashion.

Point 3—The cryo-fixation liner of point 1, wherein the cryo-fixation liner is disposed within an inner lumen within the lead extraction catheter, such that it lines the internal surface of the lumen.

Point 4—The cryo-fixation liner of point 1, wherein the cryo-fixation liner is compatible with any number of cryogens and cryoconsoles, for example, subcooled nitrogen, pressurized subcooled nitrogen, carbon dioxide, argon, nitrous oxide, and others.

Point 5—The cryo-fixation liner of point 1, wherein the cryogen is provided to a cryogen spray nozzle at the distal tip of the lead extraction catheter.

Point 6—The cryo-fixation liner of point 1, wherein the cryogen is provided to a distal cooling chamber at the distal tip of the lead extraction catheter, and wherein the cryo-fixation liner further includes at least one return line for conducting used cryogen away from the distal cooling chamber for recovery.

Point 7—A lead extractor catheter having supply and return lines and a distal cooling chamber integrated into the lead extractor catheter itself.

Point 8—A cryo-fixation device including either an internal or external cryo-fixation liner, or integrated supply and return lines and cooling chamber within the lead extractor catheter itself.

Point 9—A cryoconsole for delivering liquid and/or gaseous cryogen to a cryoprobe, such as the cryo-fixation cardiac pacemaker lead extraction device.

Point 10—A cryo-fixation system including a cryoconsole in fluid connection with a lead extraction device, the device containing supply and return lines (or lumens).

One example of a suitable workflow or sequence of operation for lead extraction is provided below. (It is noted that leads that have been in place for over a year will often require power extraction tools, such as those disclosed herein, for removal.)

- The pacemaker/defibrillator pocket is opened, which is usually just under the skin in the left pectoral region
- The leads are unscrewed from the pacemaker/defibrillator and dissected from scar tissue down to where they insert into the vasculature
- If it is an active fixation lead (i.e. the distal end contains a screw that extends into the cardiac myocardium), a wrench is used to retract the distal helix from the myocardium
- The proximal end of the lead (i.e. outside the pocket) is cut to expose the inner lumen of the lead
- A locking stylet is placed in the lead (locking stylet is different than a normal stylet in that it expands when in the lumen to aid in traction in the distal portion of the lead body)
- Sutures are used to tie the outer insulation (and inner wires) to the locking stylet so the entire lead can be pulled as one
- The lead/locking stylet/suture system is fed through the cryo-fixation lead extraction device 100
- As the cryo-fixation lead extraction device 100 is advanced in the vasculature, counter-traction is applied to the lead
  (a) Advancing/rotating the sheath over the lead in the vasculature will sometimes free portions of the lead without applying additional cryo/thermal and/or mechanical energy to cut the lead free from the patient tissue
- When the sheath cannot be advanced by manual advancing/rotating, the cryo/thermal and/or mechanical energy is applied to the lead with counter-traction.
  a. There may be a desire to be cognizant of the amount of traction being applied
  b. There may be a desire to have enough working lumen inside the sheath, so that the lead does not cause increased friction on the sheath as it is being advanced, so that the operator can have precise control of movement of the cryo-fixation lead extraction device 100 over the lead c. Lead extraction size consideration: There may be a desire to have enough gap between lead and liner lumen or catheter lumen size as to avoid friction when advancing, to give operator greater control without "stuttering" or "catching" of the lead within the liner or catheter lumen While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A cryo-fixation lead extraction device comprising: a lead extraction catheter having longitudinally spaced proximal and distal catheter ends and an elongate catheter lumen; a liner having longitudinally spaced proximal and distal liner ends and an elongate liner lumen, the liner lumen extending entirely between the proximal and distal liner ends and being configured to selectively accept at least part of a lead being extracted longitudinally therethrough, at least a portion of the liner being located a chosen one of circumferentially within and circumferentially surrounding the catheter lumen; and at least one cryogen supply line extending longitudinally through at least a portion of the liner lumen, the cryogen supply line being configured to place a cryogen fluid source in operative proximity to the proximal liner end in fluid communication with the distal liner end, the cryogen supply line being configured to selectively generate a patient tissue frozen zone adjacent the distal catheter end, wherein the at least one cryogen supply line is affixed to an inner surface of the liner lumen; and a cutting feature located adjacent the distal catheter end, the cutting feature configured to selectively mechanically cut into at least a portion of the patient tissue frozen zone adjacent the lead being extracted.

2. The cryo-fixation lead extraction device of claim 1, wherein the liner is configured for rotational movement with respect to the catheter lumen.

3. The cryo-fixation lead extraction device of claim 1, including
a distal freezing chamber located adjacent the distal liner end and being in fluid communication with the cryogen fluid source via the at least one cryogen supply line; and
at least one cryogen return line extending longitudinally through at least a portion of the liner lumen, the at least one cryogen return line being configured to place the distal freezing chamber in fluid communication with a cryogen fluid destination via the proximal liner end;
the cryogen fluid source, the at least one cryogen supply line, the distal freezing chamber, the at least one cryogen return line, and the cryogen fluid destination collectively comprising a closed cryogen loop preventing passage of cryogen fluid distally from the cryo-fixation lead extraction device.

4. The cryo-fixation lead extraction device of claim 3, wherein the liner at least partially circumferentially surrounds the lead extraction catheter, with the at least one cryogen supply line and the at least one cryogen return line at least partially interposed radially between the liner and the lead extraction catheter.

5. The cryo-fixation lead extraction device of claim 3, wherein the lead extraction catheter at least partially circumferentially surrounds the liner.

6. The cryo-fixation lead extraction device of claim 1, wherein the cutting feature is located on a selected one of the distal catheter end and the distal liner end, and the lead extraction catheter is configured for at least one of oscillational motion relative to the liner and rotational motion about a longitudinal axis relative to the liner.

7. The cryo-fixation lead extraction device of claim 1, wherein the lead extraction catheter and the liner are integrally formed as a single tube.

8. The cryo-fixation lead extraction device of claim 1, wherein a temperature of at least a portion of the patient tissue frozen zone is in the range of −5° C. to −30° C.

9. A cryo-fixation lead extraction system comprising: a cryogen fluid source; a cryo-fixation lead extraction device including a lead extraction catheter having longitudinally spaced proximal and distal catheter ends and an elongate catheter lumen, a liner having longitudinally spaced proximal and distal liner ends and an elongate liner lumen, the liner lumen extending entirely between the proximal and distal liner ends and being configured to selectively accept at least part of a lead being extracted longitudinally therethrough, and at least a portion of the liner being located a chosen one of circumferentially within and circumferentially surrounding the catheter lumen, at least one cryogen supply line extending longitudinally through at least a portion of the liner lumen, the cryogen supply line being configured to place a cryogen fluid source in operative proximity to the proximal liner end in fluid communication with the distal liner end, the cryogen supply line being configured to selectively generate a patient tissue frozen zone adjacent the distal catheter end, wherein the at least one cryogen supply line is affixed to an inner surface of the liner lumen, and a cutting feature located adjacent the distal catheter end, the cutting feature configured to selectively mechanically cut into at least a portion of the patient tissue frozen zone adjacent the lead being extracted; a cryogen regulator associated with the cryogen fluid source; an operator interface operatively connected to the cryogen supply line for selectively regulating cryogen fluid flow; and a computing device for at least one of controlling and monitoring the cryo-fixation lead extraction device during operation, the computing device including a user-perceptible display and at least one user-manipulable control.

10. The cryo-fixation lead extraction system of claim 9, including a cryogen fluid destination, and wherein the cryo-fixation lead extraction device includes
a distal freezing chamber located adjacent the distal liner end and being in fluid communication with the cryogen fluid source via the at least one cryogen supply line, and
at least one cryogen return line extending longitudinally through at least a portion of the liner lumen, the at least one cryogen return line being configured to place the distal freezing chamber in fluid communication with a cryogen fluid destination via the proximal liner end;
the cryogen fluid source, the at least one cryogen supply line, the distal freezing chamber, the at least one cryogen return line, and the cryogen fluid destination collectively comprising a closed cryogen loop preventing passage of cryogen fluid distally from the cryo-fixation lead extraction device; and
the operator interface being operatively connected to at least one of the at least one cryogen return line and the cryogen fluid destination for selectively regulating cryogen fluid flow.

11. The cryo-fixation lead extraction system of claim 9, including a portable mounting frame configured to support and transport the cryogen fluid source, cryogen regulator, operator interface, and computing device.

12. The cryo-fixation lead extraction system of claim 9, wherein a temperature of at least a portion of the patient tissue frozen zone is in the range of −5° C. to −30° C.

13. A cryo-fixation lead extraction liner comprising: longitudinally spaced proximal and distal liner ends and an elongate liner lumen, the liner lumen extending entirely between the proximal and distal liner ends and being configured to selectively accept at least part of a lead being extracted longitudinally therethrough; at least one cryogen supply line extending longitudinally through at least a portion of the liner lumen, the cryogen supply line being configured to place a cryogen fluid source in operative proximity to the proximal liner end in fluid communication with the distal liner end, the cryogen supply line being configured to selectively generate a patient tissue frozen zone adjacent the distal liner end, wherein the at least one cryogen supply line is affixed to an inner surface of the liner lumen; and a cutting feature located adjacent the distal liner end, the cutting feature configured to selectively mechanically cut into at least a portion of the patient tissue frozen zone adjacent the lead being extracted.

14. The cryo-fixation lead extraction liner of claim 13, wherein at least a portion of the liner is located circumferentially within a lead extraction catheter with which the liner is associated.

15. The cryo-fixation lead extraction liner of claim 13, wherein at least a portion of the liner is located circumferentially surrounding a lead extraction catheter with which the liner is associated.

16. The cryo-fixation lead extraction liner of claim 13, including
a distal freezing chamber located adjacent the distal liner end and being in fluid communication with the cryogen fluid source via the at least one cryogen supply line; and
at least one cryogen return line extending longitudinally through at least a portion of the liner lumen, the at least one cryogen return line being configured to place the distal freezing chamber in fluid communication with a cryogen fluid destination via the proximal liner end;
the cryogen fluid source, at least one cryogen supply line, the distal freezing chamber, at least one cryogen return line, and the cryogen fluid destination collectively comprising a closed cryogen loop preventing passage of cryogen fluid distally from the cryo-fixation lead extraction liner.

17. The cryo-fixation lead extraction liner of claim 13, wherein a temperature of at least a portion of the patient tissue frozen zone is in the range of −5° C. to −30° C.

18. A method of extracting a lead from a patient tissue volume using cryogenics, the method comprising: providing a cryo-fixation lead extraction device including a lead extraction catheter having longitudinally spaced proximal and distal catheter ends and an elongate catheter lumen, a liner having longitudinally spaced proximal and distal liner ends and an elongate liner lumen extending entirely between the proximal and distal liner ends, at least a portion of the liner being located a chosen one of circumferentially within and circumferentially surrounding the catheter lumen, at least one cryogen supply line extending longitudinally through at least a portion of the liner lumen, wherein the at least one cryogen supply line is affixed to an inner surface of the liner lumen, and a cutting feature located adjacent the distal catheter end; with the cryogen supply line, placing a cryogen fluid source, which is in operative proximity to the proximal liner end, into fluid communication with the distal liner end; placing at least part of a lead being extracted longitudinally through the liner lumen; selectively directing cryogen fluid from the cryogen fluid source through the cryogen supply line to selectively generate a patient tissue frozen zone adjacent the distal catheter end within the patient tissue volume; with the cutting feature, selectively mechanically cutting into at least a portion of the patient tissue frozen zone adjacent the lead being extracted to loosen the lead from the patient tissue; and moving the loosened lead proximally with respect to the liner lumen.

19. The method of claim 18, including:
providing the cryo-fixation lead extraction device with a distal freezing chamber located adjacent the distal liner end and at least one cryogen return line extending longitudinally through at least a portion of the liner lumen;

placing the distal freezing chamber in fluid communication with the cryogen fluid source via the at least one cryogen supply line;

with the cryogen return line, placing a cryogen fluid destination, which is in operative proximity to the proximal liner end, into fluid communication with the distal freezing chamber; and preventing passage of cryogen fluid distally from the cryo-fixation lead extraction device through use of a closed cryogen loop comprised of the cryogen fluid source, at least one cryogen supply line, distal freezing chamber, at least one cryogen return line, and the cryogen fluid destination.

20. The method of claim 18, including:

passing a stylet longitudinally into the liner lumen;

securing the stylet to the lead being extracted; and exerting proximally directed longitudinal force on the stylet to assist with moving the loosened lead proximally with respect to the liner lumen.

\* \* \* \* \*